United States Patent [19]
Windle

[11] Patent Number: 5,707,797
[45] Date of Patent: Jan. 13, 1998

[54] COLOR IMAGING METHOD FOR MAPPING STRETCHED DNA HYBRIDIZED WITH FLUORESCENTLY LABELED OLIGONUCLEOTIDE PROBES

[75] Inventor: Bradford E. Windle, San Antonio, Tex.

[73] Assignee: CTRC Research Foundation, San Antonio, Tex.

[21] Appl. No.: 264,802

[22] Filed: Jun. 23, 1994

Related U.S. Application Data

[63] Continuation-in-part of PCT/US94/00340, Jan. 10, 1994, which is a continuation-in-part of Ser. No. 2,781, Jan. 8, 1993, abandoned.

[51] Int. Cl.$^6$ .................................................. C12Q 1/68
[52] U.S. Cl. ............................. 435/6; 435/6; 935/77; 935/78
[58] Field of Search ..................... 435/6, 91.1; 935/78, 935/87; 382/129, 191

[56] References Cited

U.S. PATENT DOCUMENTS

| | | | |
|---|---|---|---|
| 4,741,043 | 4/1988 | Bacus | 382/6 |
| 4,994,373 | 2/1991 | Stavrianopoulos et al. | 935/87 |
| 5,192,683 | 3/1993 | Price et al. | 435/240.27 |
| 5,405,747 | 4/1995 | Jett et al. | 435/91.1 |
| 5,470,709 | 11/1995 | Heng et al. | 935/78 |
| 5,470,710 | 11/1995 | Weiss et al. | 435/6 |

OTHER PUBLICATIONS

Burke et al., "Cloning of Large Segments of Exogenous DNA into Yeast by Means of Artificial Chromosome Vectors," *Science*, 236:806–812.

Burmeister and Lehrach, "Long–range restriction map around the Duchenne muscular dystrophy gene," *Nature*, 324:582–585, 1986.

Cangiano et al., "Use of repetitive DNA probes as physical mapping strategy in Caenorhabditis elegans," *Nucleic Acids Research*, 18(17):5077–5081, 1990.

Coulson et al., "Genome linking with yeast artificial chromosomes," *Nature*, 335:184–186, 1988.

Evans and Lewis, "Physical mapping of complex genomes by cosmid multiplex analysis," *Proc. natl. Acad. Sci. USA*, 86:5030–5034, 1989.

Lawrence et al., "Interphase and Metaphase Resolution of Different Distances Within the Human Dystrophin Gene," *Science*, 249:928–932.

Lichter et al., "Fluorescence in situ hybridization with Alu and L1 polymerase chain reaction probes for rapid characterization of human chromosomes in hybrid cell lines," *Proc. natl. Acad. Sci. USA*, 87:6634–6638, 1990.

Kallioniemi et al., "Comparative Genomic Hybridization for Molecular Cytogenetic Analysis of Solid Tumors," *Science*, 258:818–821, 1992.

Poustka et al., "Construction and use of human chromosome jumping libraries from NotI–digested DNA," *Nature*, 325:353–355, 1987.

Stallings et al., "Physical mapping of human chromosomes by repetitive sequence fingerprinting," *Proc. Nalt. Acad. Sci. USA*, 87:6218–6222, 1990.

Trask et al., "The Proximity of DNA Sequences in Interphase Cell Nuclei is Correlated to Genomic Distance and Permits Ordering of Cosmids Spanning 250 Kilobase Pairs," *Genomics*, 5:710–717, 1989.

Weber and May, "Abundant Class of Human DNA Polymorphisms Which Can Be Typed Using the Polymerase Chain Reaction," *Am. J. Hum. Genet.*, 44:388–396, 1989.

Windle et al., "A central role for chromosome breakage in gene amplification, deletion formation, and amplicon integration," *Genes & Development*, 5:160–174, 1991.

Yagle et al., "Genetic and physical map of the von Recklinghausen neurofibromatosis (NF1) region on chromosome 17," *Proc. Natl. Acad. Sci. USA*, 87:7255–7259, 1990.

Matsumoto et al. (1981) & Mol. Biol. 152:501–516.

Windle et al. (Apr. 1993) Cancer Genetics and Cytogenetics 66 (2):144.

Parra et al. Nature Genetics 5 (Sep. 1993):17–21.

*Primary Examiner*—Lisa B. Arthur
*Attorney, Agent, or Firm*—Arnold, White & Durkee

[57] ABSTRACT

The present invention relates generally to the fields of macromolecule image analysis and interpretation. More particularly, it concerns means for selecting an image, and using unique color vector computer automation to determine the shape, length, and physical characteristics of a stained DNA image midline based on the overall contour. The invention also includes methods of gravitationally stretching DNA to an essentially linear, 2-dimensional form having an inter kilobase pair distance of between 0.34 µm to 0.65 µm per kilobase pair. Examples of color images analyzed are presented and include the mapping of DIRVISH stained DNA markers, orientation, and distances. A novel use of the method allows determination of replication origin and termination sites on the DNA.

25 Claims, 7 Drawing Sheets

COLOR IMAGING METHOD FOR MAPPING STRETCHED DNA HYBRIDIZED WITH FLUORESCENTLY LABELED OLIGONUCLEOTIDE PROBES

This is a continuation in part application of PCT application Ser. No. US 94/00340 filed Jan. 10, 1994 which is a continuation in part application of U.S. patent application Ser. No. 08/002,781 filed Jan. 8, 1993 now abandoned.

BACKGROUND OF THE INVENTION

1. Field of the Invention

The present invention relates to the measurement of physical distances within intact extended and super-extended DNA, methods of producing the extended DNAs and to efficient and rapid mapping of genes and other sequences employing various forms of extended DNA and DNA probes, particularly for visual mapping such as where fluorescent hybridization (comparable to in situ hybridization techniques) is employed. More particularly, it concerns a color imaging system whereby the image of a complex macromolecule is measured using color vector analysis to provide information concerning physical characteristics including shape, length, orientation, and size are determined. The invention allows the detection, identifying and mapping of origins of replication.

2. Description of the Related Art

Current DNA imaging technology, such as computer aided pattern recognition systems, lack the means to fully extract and analyze information in their native light wavelengths, nor has technology been developed that is capable of finding the midline of complex DNA color-image contours. Such a system would be useful in the determination, analysis, and direct visualization of physical genomic maps used for the identification of genes and DNA sequences, orientation and relative distances.

A primary goal in developing a genome map is the identification of genes and DNA sequences involved in disease states or disorders as well as in normal functions of the cell. The direct physical mapping of genes that may be responsible for disease states or disorders linked to specific genetic markers is a key aspect of the genome project. The combined use of genetic and physical mapping of the human genome has proven useful in the placement of genes and/or molecular markers in reference to each other and in the cloning and identification of genes of biological and medical significance. However, current methods for the identification of map distances require the use of genetic linkage data in a population to connect a disease or biological characteristic with molecular DNA markers. With this information, a physical map can be used to identify a gene of interest by its position in relation to the DNA markers.

The characterization of gene structure and genome organization has been greatly facilitated by the development of a number of physical mapping technologies including restriction mapping and DNA sequencing. Techniques, such as the "fingerprinting" of repetitive elements (Litt, et al. 1989), have been developed to fill in for long range restriction mapping deficiencies.

The use of in situ hybridization (FISH) to identify the position of probes on metaphase chromosomes (Weber, et al. 1989) allows the rapid mapping of DNA probes with approximately 1 Mb resolution. For higher resolution mapping, the FISH technique has been applied to interphase nuclei (Evans, et al. 1989). Since the DNA is less condensed in interphase nuclei than in metaphase chromosomes, resolution in the 50–100 Kb range can be obtained. However, mapping the distance between two probes in three dimensional nuclei or compressed two dimensional nuclei is complex and requires large data sampling and probability calculations based on a random walk model (Coulson, et al. 1988).

Chromosome jumping was devised to permit the cloning of DNA from both ends of a NotI fragment (separated by many hundreds of Kb) without chromosome walking (Poustka, et al. 1987). However, the development of yeast artificial chromosomes (YACs) for cloning genomic DNA as large as 1 Mb (Burke, et al. 1987) has circumvented this approach, since chromosome jumping does not identify DNA between the jump; nevertheless, cosmid clones are still used for many types of probes and for sequencing, since there are not adequate means for purifying YAC DNA in substantial quantities. The combined use of cosmids and YACs has provided one of the more effective approaches to genome mapping (Coulson, et al. 1988).

There are, however, many drawbacks to this combined technique in genome mapping. While it is a simple matter to determine whether a particular cosmid (or cosmids) contains DNA represented within a YAC or a chromosomal region, it is necessary to construct a restriction map of the YAC to determine the location of the cosmid sequences within the YAC or to determine the relative positions of multiple cosmids. On a larger scale, the relative positions of multiple YACs is also unnecessary. Stallings, et al. (1990), have developed a fingerprinting strategy using repetitive sequence hybridization to restriction fragments for determining overlap of two cosmids or YACs (Cangiano, et al. 1990). However, if the clones do not overlap, a more involved mapping strategy is needed.

Long distance restriction maps of DNA regions have been generated using rare cutting restriction enzymes such as NotI (Poustka, et al. 1987; Yagle, et al. 1990; Barmeister, et al. 1986). NotI linking clones, which encompass a NotI cleavable site, have been used to facilitate NotI mapping by identification of contiguous NotI fragments (Wallace, et al. 1989). The use of frequent-cutting enzymes such as HindIII is not practical for mapping megabase-size DNA due to the complexity of the map.

Additional strategies for gathering physical linkage information on a still larger scale include the use of interspecific somatic cell hybrids, in which panels of rodent/human hybrid cell lines that retain various combinations of human chromosomes or parts thereof are used to localize probes to individual chromosomes or chromosomal regions (Ruddle, et al. 1971). Radiation-induced hybrids, in which fragments of human chromosomes are retained in a rodent cell background (Goss, et al. 1975) have also been employed.

Finally, fluorescent in situ hybridization (FISH) has become popular for determining approximate distances greater than 1 Mb between two or more probes on metaphase chromosomes (Lichter, et al. 1990). FISH may also be used to a limited extent to determine the relative order of probes. For example, more closely linked probes along a 250 Kb region have been hybridized to uncondensed DNA in interphase nuclei (Trask, et al. 1989). While information concerning order may be obtainable with such method, there are some serious shortcomings; a major problem is that DNA in interphase nuclei is three dimensional. Labels that are not closely spaced or which are in reverse order to the observed order may be inaccurately determined because labels appear to be on top of one another, or because a twisted loop is viewed two-dimensionally.

A second shortcoming is the resolution. While improvements have been made, expected resolution with FISH visualization is claimed to be about 10 Kb, although not substantiated. Resolution at 21 kbp has been reported (Heng, et al. 1992). It is thought that higher resolution is hampered because of the 3-D structure of the DNA, with lack of accessibility leading to poor resolution and difficulty in detection.

There have been other attempts to reach levels of resolution around 10 Kb; in one instance by expelling long 200 μm loops from the nucleus (van Ommen, et al. 1992), releasing chromatin fibers (Heng, et al. 1992) or creating nuclear "halos" by extending DNA from which histones have been extracted (Lawrence, et al. 1992). Although believed possible to extend resolution below 10 Kb, there do not appear to be published data demonstrating that such resolution has been achieved.

An additional need is to develop and automate physical mapping techniques in order to eliminate the tremendous amount of time and effort needed for restriction mapping and Southern blot hybridization and to increase the resolution limitation associated with FISH methods. Desirable new methods would allow microscopic visualization of cosmids or other DNA probes hybridized to an uncondensed fully extended DNA molecule and the automation of such an analysis. Mapping of specific probes with high resolution exceeding 5 Kb on YAC DNA would be possible. Finally, automating direct visual mapping of repetitive DNA elements along a DNA strand would provide a significant improvement and alternative to restriction mapping and fingerprinting techniques.

Current technology handles images in one of two ways; either the images are analyzed viewed in black and white or, multiple filtered black and white images are pseudo-colored with user defined green, red and blue, and combined into one artificially colored image for viewing. Increased sensitivity is required for complex analysis of color images, for example, that of mapping restriction fragments. Similar sensitivity is necessary for improving the analysis of short and long range gene mapping using techniques such as chromosome walking and jumping and, physical linkage determination, however, present efforts toward automating such procedures have failed to improve the speed and veracity of direct physical mapping.

SUMMARY OF THE INVENTION

The present invention overcomes these and other drawbacks inherent in the prior art by providing means to determine relative distance between DNA markers, thereby identifying the relative location and distance between sites on the same strand of DNA. This is accomplished by combining fluorescent hybridization and computer aided imaging. The invention encompasses a novel computer aided approach to digitize the DNA image in color, determine the midline of the DNA contour, tracking colorimetric changes along the midline and cross-section in the image, to determine the relative distance between markers, and assessing the minute nuances that are intrinsic to DNA color images.

Accordingly, in one aspect, the novel methods of the present invention provide for precision analysis and determination of distances from DNA maps created by a novel direct visualization technique. This technique employs extended or super-extended DNA hybridized with probes suitably labeled for detection. The term "distance" as used herein, is used to describe the length of a DNA color image as automatically determined by the present invention. The term "midline" as used herein, is used to describe the central axis of the DNA color image as automatically determined by the present invention. The term "mapping" as used herein, describes determining the relative position, distance, orientation, size, number, presence, or other physical characteristics known to those skilled and versed in the art, of genetic markers on a strand of DNA.

In a related aspect of the present invention, standard direct visualization hybridization (DIRVISH) or fluorescence in situ hybridization (FISH) derived images are analyzed by direct visualization of the DNA under the microscope with resolutions as low as 0.4 Kb. Other fluorescence visualization methods, or variations thereof, such as scintillography, radiography, chemoluminescence, chromagenicity, fluorescence, etc. can also be analyzed. The analysis of extended or super-extended DNA using the present invention provides significantly increased resolution and greatly reduced analysis time.

The invention also includes a system employing a novel "Autoline" program and its derivatives (collectively called ColorTrak). The programs are written in J language, a set of commands that specifically operates the Oncor V150 imaging system. The inventors have developed programs that utilize the V150 software to interface with two V150 computer boards that retain the image for analysis. The programs encompass the complete control of the computer boards, the attached CCD camera, and all analytical procedures operated through mouse operated menus. The same programming may also employ any number of computer languages, e.g., C language using Oncor's C language interface. Alternatively, the same programming is possible using other commands that can direct color image analysis in other imaging systems.

In addition to a complete menu operation, there are specific functions of the programs used to automate the invention that are conceptually unique. The programs of the invention analyze colored objects, typically fluorescent images generated by either the DIRVISH technique or the FISH technique. A pixel by pixel, section by section, and object by object color spectrum reading and analysis of strings or "blobs" of signal is generated. This reading allows for the precise determination of the length of the strings as determined from the collected data, which represents the axial midline of the string. The data may also be stored and retrieved for further analysis. The V150 imaging system uses a unique color space model to define color that allows for the complex mathematical definitions and manipulations required to increase the resolution and to automate the genetic mapping of DNA segments.

There are unique advantages of the disclosed invention that are useful for precision DNA mapping. The color analysis permits the use of either one or several hybridization probes in order to determine the distance between two sites; thus, a restriction map of a DNA region (e.g., a YAC clone or genomic DNA) is no longer necessary for determining the distance between two probes. Additionally, the method of the invention permits analysis of minute amounts of DNA, e.g., 100 molecules or from about 1 femtogram to 1 nanogram depending on the genome size. Information is acquired rapidly enabling determination in days, rather than weeks, months or even years in some cases using standard DNA mapping procedures. Chromosomal DNA can be mapped directly, thus avoiding mapping errors due to possible rearrangements in the clones. Large scale mapping distances between two probes is possible, with limitations based on the size of intact DNA maintained by standard preparation procedures.

Repetitive sequence probes, (e.g., L1, Alpha, or Alu repeats) may be analyzed and a repeat map generated, providing an alternative to the more involved, time consuming, and complex task of mapping restriction sites. It also provides increased sensitivity and is a vast improvement over current fingerprinting. Yet another advantage of the method is the ability to simultaneously determine the position of a specific sequence probe relative to a repeat map.

The present invention allows for the direct microscopic visualization required to determine the relative order and distance of images, e.g., between DNA segments or probes. This distance represents, and is directly correlateable to codetermined known distances providing the resolution, in kilobase pairs per μm. The known distance standards can include intrinsic distance standards, heterologous DNA standards, or other staining procedures known to those of skill in the art of DNA staining and mapping.

The color image analysis methods of the present invention also permit determination of the relative position of various markers that have been differentially labeled; for example, with one, two, three, or more different fluorescent probes that are visualized under the microscope as different colors. Visualization need not be by fluorescent microscopy. Other such methods, such as, light microscopy or scintillography, can be used for detection.

The inventors have developed methods for stretching DNA strands in a virtual straight line across a slide and for use in hybridization of fluorescent probes. The result is a stream of DNA threads, which are invisible unless counterstained, and threads of multicolor fluorescent signals from the different probes. This procedure, is referred to as DIRVISH (direct visual hybridization) DNA mapping. The inventors have studied long range maps of >500 Kb, and short range high resolution maps of ~5 Kb, obtaining a resolution as low as 0.4 Kb. Therefore, it is possible to map distances, overlap, gaps and orientation of probes using this procedure.

The present invention provides a means of generating high resolution maps of YACs within a contig and closely linked YACs. Three probe hybridization using combinations of different fluorochromes has been demonstrated; however, using the same procedure it is readily apparent the simultaneous analysis of 9 or more probes is possible. The present invention greatly increases the speed and accuracy of analysis. The procedure and analysis requires only 2 days, and provides more information than comparable Southern blot analysis, without the need for extensive knowledge of the site under study.

Analysis of overlap between YACs by current procedures, which requires pattern recognition of either inter-Alu PCR products or repetitive sequences containing restriction fragments, is dependent on the presence of repetitive sequences. The uncertainty of pattern recognition and the potential for absence of repetitive sequences makes these procedures less desirable compared to the direct visual procedure as interpreted by the product of the present invention. The extent of overlap as measured by the current procedures is also not necessarily accurate, depending on how evenly dispersed the repetitive sequences are located throughout the YAC sequences.

Employing the methods of the present invention, one is able to obtain information from stained YACs not available by current procedures, including detecting deletions in a YAC as compared to the genomic sequence. Precise gap distance between closely linked YAC contigs can also be determined. With current procedures, this information can be determined only by long range restriction mapping or chromosome walking.

The present invention allows one to map several probes, each labelled with different fluorescent colors for simultaneous mapping. A method for painting chromosomes with 12 colors has already been published (Duawerse, et al. (1992)). However, mapping accuracy and speed could be dramatically increased using the described methods to map 12-color labeled DNA.

Particular applications in research include rapid mapping of restriction fragments in the genome or cosmid, mapping orientation of cosmid to any other probe site, mapping one cosmid to another cosmid (overlap or gap), mapping restriction fragments in YACs, YAC to YAC (overlap or gap), or orientation of YAC to another probe site, mapping sites of exons >0.4 Kb in a gene using cDNA probes, mapping sites of PCR products such as inter-alu PCR, producing unique patterns for specific regions, mapping unique patterns for specific regions, mapping repeats such as Alu or Line or Alpha in specific regions, producing unique patterns as a map for ubiquitous repeats (Alu or Line) mapping on YACs directly from yeast cells or genome fragments from somatic or radiation hybrids, mapping unique probes from NotI linking or jumping library or related systems, detecting rearrangements, for example, inversions, deletions, etc. in cosmids, YAC clones by comparison to genomic DNA, mapping rearrangements in genes for diagnostic significance.

The system for color imaging developed for the present invention is intended to complement multicolor probe procedures by tracking DNA strands while recognizing and distinguishing any array of colors. The system and methods will also have application in tracing through chromosomes for analysis by multi-color comparative genomic hybridization procedures, such as that described by Kallioniemi, et al. (1992).

An important further aspect of the invention is its use as a method of detecting, identifying and mapping origins of replication. One may clone a specific origin and also measure functioning of specific origins when perturbed by inhibitors. This is possible even when a clone of the origin is not available.

The availability of a method to identify origins of replication and termination allows identification, mapping and cloning of any origin of replication that is within about 500 Kb of a DNA probe. The origins identified could be targets for anti-cancer therapeutics, for example, or as candidates for artificial chromosome constructs. Similarly, one may identify and clone origins of termination. This method provides an origin-specific assay for studying the ability to initiate and elongate at a particular origin and the origin-specific inhibition by drugs, some of which could be of therapeutic value. Likewise, the method provides a termination site-specific assay for studying drugs that affect termination. These also could be of therapeutic value.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG 1A shows an irregular shaped object in black on a grid in a white background (lower left), and FIG 1B shows the method of tracking the object on a pixel grid to follow the image using a hierarchical rendition of the initial vectors (A through H). The longest vector is determined and this defines the direction of advancement. Starting at the pixel shown, vector A represents the longest vector and once determined only vectors C and G are evaluated (as shown on the right). The furthest points in the object along vectors C and G are determined and the mathematical center between those two coordinates indicates the initial midpoint. Based on this determination the first midpoint of the midline for the complex contour length is recorded and stored.

FIG 2A shows the irregular shaped object in black on a grid in a white background (lower left), and FIG 2B shows the method for tracking the object on a pixel grid following the determination of a new longest vector is shown (Vector H). Starting at pixel position seven, vector H represents the longest vector and the new direction of advancement. Once determined only vectors B and F are evaluated. Based on this determination the next midpoint of the midline for the complex contour length is calculated and stored.

In FIG. 6A the string of signal was analyzed for color and coordinate position. A tracing line, shown below it, shows how the string of signal was traced. FIG. 6B shows a graph of one dimensional color values customized for red to green analysis only.

DETAILED DESCRIPTION OF THE PREFERRED EMBODIMENTS

Figures 1A, 1B:
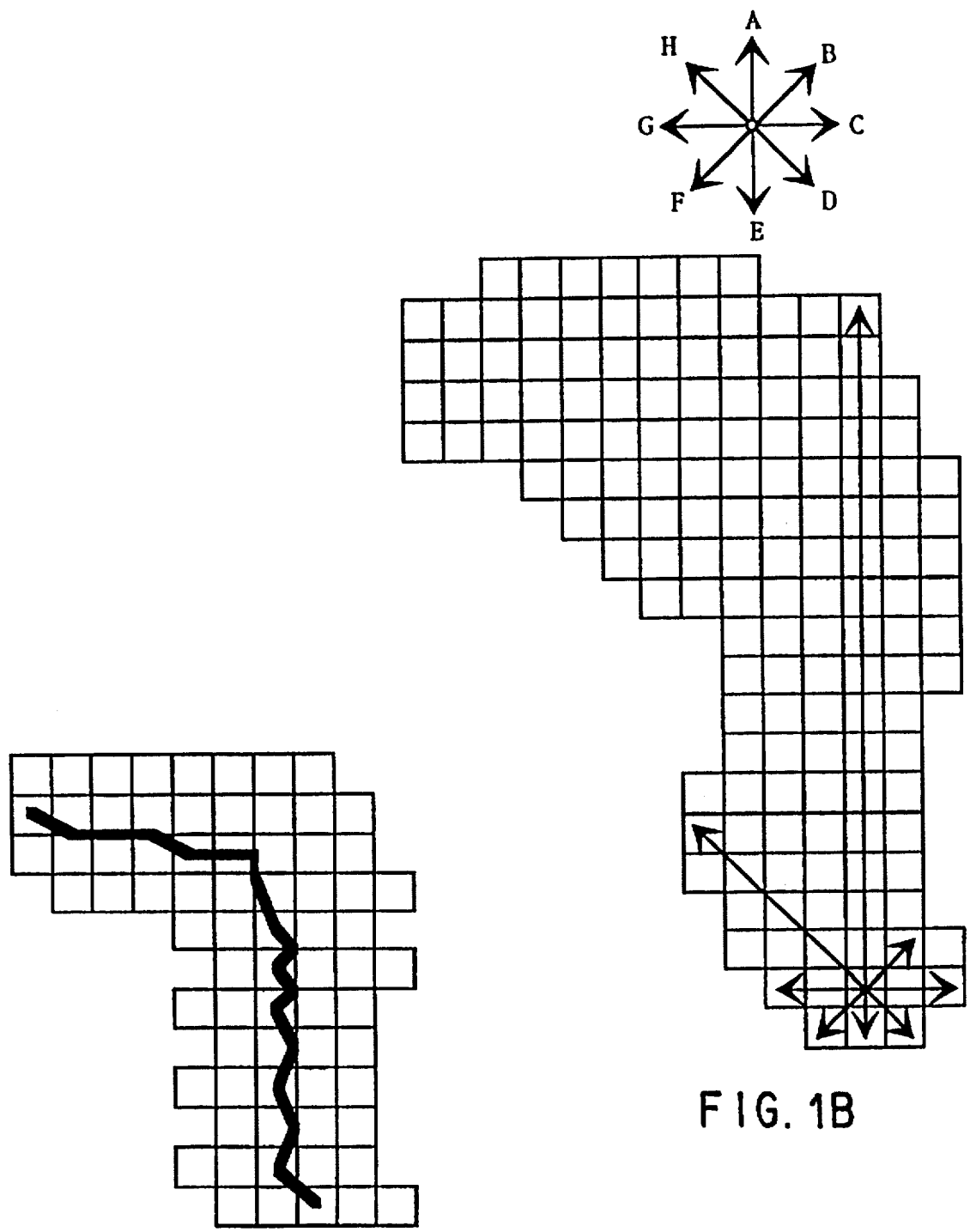
FIGS. 1A and 1B show the diagramatical representation of the initial analysis the program of the invention uses to determine the direction to follow.

The disclosed methods offer advantages over current systems for object analysis. It evaluates color images and the length of the image based on their natural wavelength emission, without filtering or modification. It also automates the gathering of information that is used to directly quantitate map distances. The methods offer greatly enhanced resolution, accuracy, in a shorter period of time.

Computer imaging systems that acquire images in shades of black and white are known as a grey scale. In these systems, the color analysis is artificial using a variety of optical filters to extract out different colors, typically, red, green, and blue. Three black and white images are then acquired through the three filters and stored. However, the variety of color shades is lost with this procedure, so that, for example, a turquoise green and a lime green both with the same intensity are indistinguishable. Color analysis with very sensitive color discrimination is necessary for the identification and analysis of, for example, genetic linkage data in a population to connect a disease or biological characteristic with molecular DNA markers of images created by fluorescence in situ hybridization. Computer analysis of this information can provide a physical map that can be used to identify a gene of interest by its position in relation to the DNA markers.

The analysis of grey objects is performed by commercially available software packages. Many of these programs are an intrinsic part of black and white imaging systems used to identify karyotypes. These programs are intrinsically deficient for the analysis of DNA images as stained in their native wavelengths, since the data is acquired through filters that remove characteristics of hue, saturation, and intensity from the image. The final pseudocolor rendition generated by overlapping grey scale images at best approximates but does not faithfully represent the original image. Finally, there are no systems or programs that can generate a linear representation of the signals with their true native colors.

The analysis of each of the three black and white images requires three times the effort than the system of the present invention with a lesser degree of sensitivity. Therefore, in addition to their major drawback of black and white data acquisition these systems lack the ability to gather, evaluate, and quantitate genetic distances in color. For example, the Imagenetics' imaging system performs the genetic analysis in black and white, and subsequently creates a pseudo-color image for display purposes. This approach severely limits the resolution of the analysis because it is unable to differentiate between different shades of the same color, due to the intrinsic limitations of gray-scale image acquisition.

There are several systems currently available that are able to acquire and process color images, e.g., Image Pro Plus by Media Cybernetics, and Optimus by Bioscan. These systems and their programs are not currently capable of aiding in the automation of genetic analysis. Such systems simply function to allow the user to analyze defined color. Furthermore, these systems have not been developed for, and are incapable of, determining the midline of a complex stained DNA contour. They are therefore incapable of automatically and objectively determining physical distances, such as those required to map and orient genetic markers on any biological macromolecule, such as images for study by direct visualization in situ hybridization (DIRVISH) and fluorescent in situ hybridization (FISH).

The lack of powerful color image analysis technology has, until now, precluded automating the complex task of the direct physical mapping of distances between genetic markers in DNA samples. These steps include: acquiring an image, selecting the relevant portions and following the complex contour of the DNA to determine a midline, calculating the distances based on known positions, and creating a direct physical map of the DNA.

The programs derived for the invention analyze colored objects, typically fluorescent DIRVISH or FISH images and generate a pixel by pixel, section by section, and object by object color spectrum reading of the signal. The midline length of the strings is determined from the data by using a unique color space model to differentiate small nuances in color, making the data amenable to mathematical definitions and manipulations. For simplicity, irregular oblong shaped objects may be shown in various shades of grey on a white background with differing shades and brightness of the color spectrum, e.g., red. The background is typically black but need only be different from the object.

The procedure for determining DNA interbase distances takes advantage of the fact that when DNA is stretched out as fully extended or in a novel super-extended form, as relaxed duplexes, the distances covering small regions of DNA are easily resolved through a light microscope (5 Kb equals 1.7 μm). The inventors have used an approach similar to the fluorescent in situ hybridization technique to fluorescently label extended DNA strands. The result is a visual multi-color map of the position of one or more probes with respect to each other or any other known marker. The relative order and of the probes, the amount of overlap or gap between probes, and their orientation can easily and rapidly be determined. DNA is stretched out on a glass slide by lysing cells with sodium dodecyl sulfate and allowing the drop of DNA to run down the slide. The DNA is stretched out as the drop runs down the slide resulting in DNA with a broad range of extension, ranging from highly condensed to as much as 200% of what is considered to be the fully extended (uncoiled form) of DNA.

The steps of the invention can be described with the following example. During FISH analysis, there may be 20 to 80 of these objects in a field, representing chromosomes, the image to be analyzed is attained by simply clicking on the object with the mouse cursor, thereby initiating the following analysis:

1. 8 vectors are used to evaluate length based on color.
2. The longest axis is determined, the midpoint of the perpendicular width is marked in that direction, and said value is stored in a data file along with color values. This constitutes a point along the midline.
3. The pixel analysis advances by determining the direction of the longest axis from the midline as characterized in the previous step and analyzes 5 vectors, e.g., A, B, C, G, and H (see FIG. 1).
4. The program senses turns when a new longest axis is found. A turn in the advancing routine is made and the analysis continues with 5 new vectors evaluated based on color values to the end of the contour, along the longest axis found.
5. The midline length is calculated based on all midpoints, and the relative positions of variant colored signals such that a green within the red is also determined.
6. The methods of the present invention employing systems using programs (collectively named ColorTrak) enable generation of a linear representation of the objects shown with full color based on cross sectional analysis (midline). Matched with the appropriate apparatus, the programs provide plots of color values on a graph to show color variations and relative distance.
7. The over-all color spectrum for each object is determined then stored or used immediately for comparison to each other.

Figure 3:
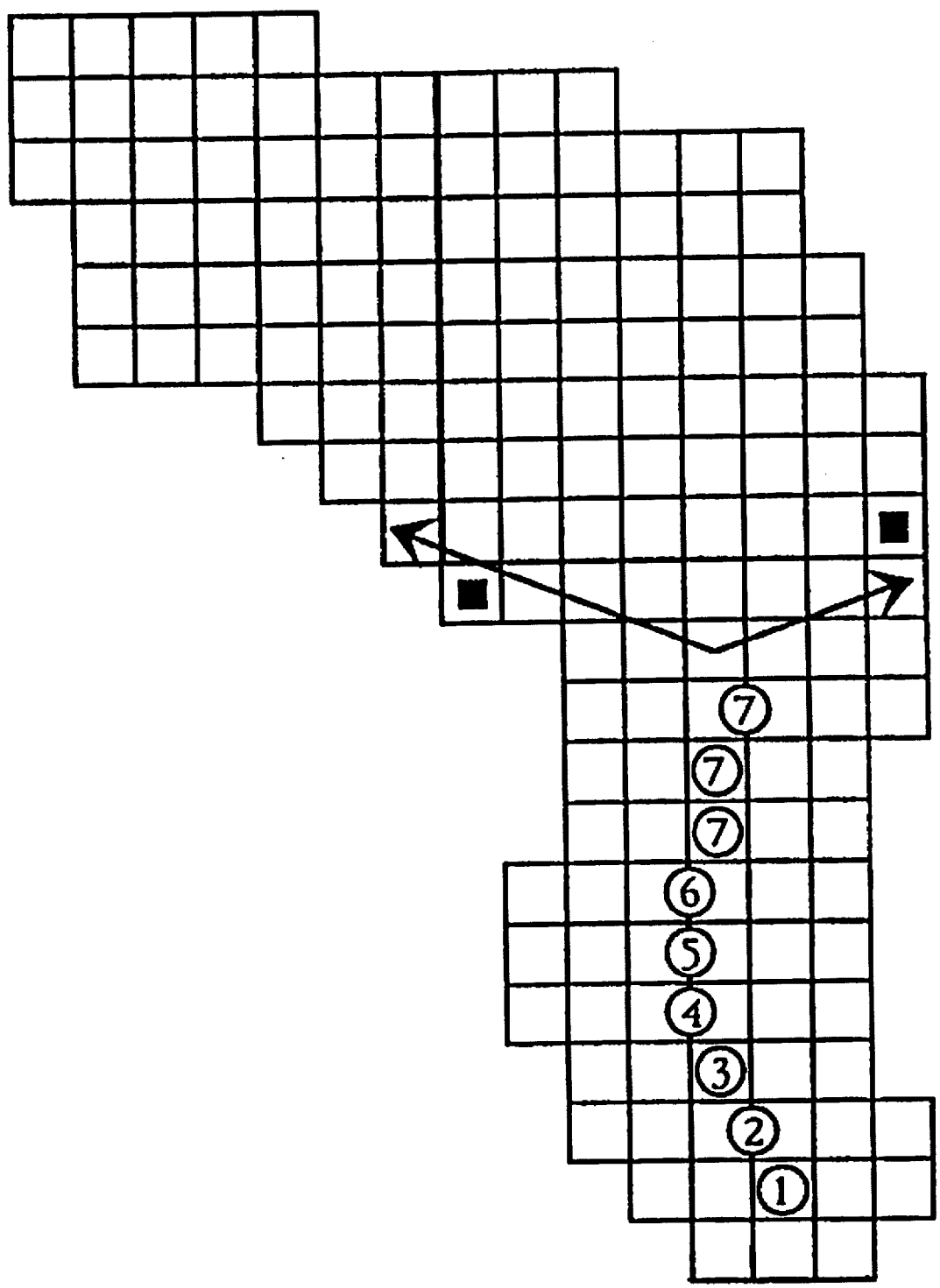
FIG. 3 shows the diagramatical representation of the image after seven midpoint determinations have been made using an alternative search method. The irregular shaped object is shown in black on a grid in a white background (lower left), and the method for tracking the object on a pixel grid following the determination of the longest vector. Two vectors are used that are at low angle to a line perpendicular to the longest vector. At pixel position seven, the next midpoint is determined from an inversion of the end pixel positions of the two vectors. Based on this determination the midline for the complex contour length is calculated and stored.

Alternatively, the inventors have also determined the midline of complex stained DNA contours by determining the midline of an object with a navigation line being generated by a two-direction analysis. The overall direction is chosen by using eight directions. After the direction with the greatest distance is determined (direction A, FIG. 3), only two directions are used. The two directions are at angles that are low compared to the line perpendicular to the direction A (e.g., an over two pixels-up one pixel progression). The midpoint is determined from the two end points of the two directions. When a turn or a curve in one direction is encountered, the direction toward that turn or curve has a greater distance and a point further along the object is found. The direction away from the turn or curve can be shorter or remain the same and thus the end point may not be as far down the object. The angle between these two points is related to the angle of the curve or turn and when inverted can be used to steer the line in the direction of the turn or curve. Thus two new end points are generated opposite to the end points originally found (shown by filled squares). The midpoint is then determined from these new points and the progression continues.

This alternative method tends to follow the curves more closely than the first method. However, it is does not sense what the direction is far ahead, in contrast to the first method which continually looks ahead.

The method for determining the midline at the end of the contour, using either of the described methods, is based on finding the last position for which the average of the pixel values perpendicular to the longest vector match or exceed the distance of said vector. This comparison can be calculated in a number of ways with the preferred average calculation representing a factor or ratio. Alternatively the Colortrak system allows for determination based on user-defined values.

The following examples are included to demonstrate preferred embodiments of the computer based stained DNA color tracking of the present invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

DETECTING AND VISUALIZING A MOLECULE OF SUPER-EXTENDED DNA

The present procedure takes advantage of the fact that when DNA is stretched out, as fully extended or super-extended relaxed duplexes, the distance covering small regions of DNA are easily resolved through a light microscope (5 Kb equals 1.7 μm). The inventors have developed a novel approach to determine physical distances along complex midline contours of fluorescent hybridization labeled extended DNA strands. The result is a visual multi-color map of the distance and position of the probes with respect to each other. The order of the probes, the amount of overlap or gap between probes, and their orientation can easily and rapidly be determined.

Direct Visualization of DNA

To map a region of DNA with this strategy, a fully extended strand of DNA must be visualized. Such visualization may be accomplished by analyzing an image following DAPI staining. Visualization of blue fluorescence through a fluorescence microscope is used to follow the migration of individual DNA strands through agarose. The mapping strategy is based on the principle that a small region of DNA (e.g., 5 Kb) when extended to the theoretical maximum for relaxed duplex DNA covers a distance visible by the light microscope. Based on the dimension of 0.34 μm per kilobase pair for β form DNA, a 5 Kb fragment would extend 1.7 μm; a 40 Kb cosmid would extend 13.6 μm, and a 500 Kb YAC would extend 170 μm. Standard or modified FISH techniques provide the means of detecting the extended DNA strands through a fluorescence microscope.

The extension of duplex DNA strands was accomplished by placing individual cells (100–5000) in two μl of PBS on one end of a glass slide and letting the drop dry. Immediately after drying 5 μl of 0.5% SDS, 50 mM EDTA, 200 mM Tris, pH 7.4 solution was placed on the dried spot to dissolve the cells and release the DNA. After 5 minutes of dissolving, the slide was tilted to allow the drop of SDS and DNA to run down the slide. This resulted in a DNA stream extending down the slide. The DNA stream was allowed to air dry and was then fixed to the slide by flooding the slide with a 75% methanol/25% acetic acid fixative. The DNA was fixed to the slide for 1–5 minutes, the excess fixative drained, and the slide air-dried. Slides were used immediately or stored in slide boxes under $N_2$ with drierite, at $-20°$ C. until used for hybridization.

DNA probes were prepared by nick translation with 30 μM of each of the four nucleotide triphosphates and 100 μm of either biotin—dUTP (BMB) or digoxigenin-dUTP (BMB) or both. The single strand size range for the probes was 100–1500 bp with 500–1000 bp being optimum with respect to high signal strength and low background. The labelled DNA was purified from unincorporated nucleotides by a Sephadex G50 spin column for biotin labelled DNA and a BioRad P60 chromatography column for the digoxigenin labelled DNA. Sephadex appeared to bind digoxigenin and is thus not suitable for purification. The enzymes were denatured with 0.05% SDS and a 5 minute 37° C. incubation prior to column purification. Nucleotide incorporation was monitored by incorporation of tracer $^{32}P\alpha dCTP$. Only probes with greater than 10% incorporation were used.

Hybridization of the probes to the DNA streams followed the general procedures described by Pinkel, et al, (1986). Slides were treated with RNAse (100 μg/ml for 30 minutes at 37° C. Slides were then placed in 70% formamide, 2× SSC at 70° C. for 3 minutes to denature the strands followed by immersion in cold 70% ethanol (2 minutes) 90% ethanol (2 minutes), 100% ethanol (2 minutes), then dried. The 20 ng of probe was mixed with 10 μg of sheared hamster DNA (100–500 bases single strand size range) and dried. The probe was resuspended in 2 μl of $H_2O$ and mixed with 8 μl of hybridization mix (69% formamide, 1.25×SSC, 12.5% dextran sulfate). The probe was denatured at 70° C. for 5 minutes then placed on ice. The 10 μl probe solution was applied to an area of the slide with the DNA stream, covered with a cover slip and sealed with rubber cement. The slide was incubated at 37° C. for approximately 18 hours. The cover slip was removed and the slide washed twice in 50% formamide, 2×SSC for 3 minutes followed by two washes in 2×SSC, all at 45° C.).

The detection of biotin was performed according to standard procedures. Avidin block (1% BSA/4×SSC, 5% Carnation non-fat dry milk) was applied to the slide and incubated at room temperature for 10 minutes. Avidin DN (Vector Labs), 5 μg/ml in 1% BSA/4×SSC was applied to the slide and incubated at room temperature for 20 minutes. The slide was washed for 2 minutes at room temperature with each of the following: 4×SSC, then 0.1% Triton ×100/4× SSC, then 4×SSC, then 0.5% NP40/0.1M $NaPO_4$ at pH 8.0. Amplification was performed by applying 4% goat serum in 0.5% NP40/0.1M phosphate buffer at pH 8.0) to the slide and incubating 10 minutes at room temperature, followed by goat biotinylated anti-avidin 5 μg/ml in 4% goat serum 0.5% NP40/0.1M phosphate buffer at pH 8.0 incubated for 20 minutes at room temperature. The slide was washed as described for the avidin procedure. Avidin block was again applied and incubated as described above. Fluorescein-avidin DN or Texas red avidin-DN (Vector Labs), 5 μg/ml in 1% BSA/4×SSC was applied to the slide and incubated for 20 minutes at room temperature. The slide was washed as described above. For immediate viewing, an anti-fade solution Vecta Shield (Vector Labs) was applied to the slide and covered by a cover slips.

The detection of digoxigenin was performed by a modified standard procedure analogous to the avidin detection. A pre-Ab block, 4% goat serum/0.5% NP40/0.1M phosphate buffer at pH 8.0 was applied to the slide for 10 minutes at room temperature. Mouse anti-digoxigenin Ab (BMB), at 10 μg/ml in pre-Ab block, was applied to the slide and incubated for 20 minutes at room temperature. The slide was washed as described for avidin detection. After a 10 minute pre-Ab block, digoxigenylated anti-mouse Ig-F(ab')$_2$ fragment, 10 μg/ml in Ab block, was applied and incubated for 20 minutes at room temperature. The slide was washed as described. After a 10 minute pre-Ab block, fluorescein or rhodamine labelled anti-digoxigenin Fab fragment was applied to the slide (25 μg/ml in Ab block) and incubated for 20 minutes at room temperature. The slide was washed as described and antifade applied.

The fluorescence microscopy used a triple band-pass filter (Omega Optical) which allows the simultaneous visualization of fluorescence by DAPI, fluorescein and Texas red or rhodamine. A Nikon Labaphot 2A and a Planapo 100×1.4 was used. Film photography was performed using Ektachrome ASA 400 slide film. CCD photography was accomplished using the American Innovision V150 color imaging system (San Diego, Calif.). CCD photography typically required only 0.5 second exposure versus a 20-second exposure for film photography.

The resulting DNA is stretched out with a broad range of extension, ranging from highly condensed to as much as 200% of what is traditionally considered to be the fully extended form DNA, i.e., an inter kilobase pair distance of 0.34 μm.

Figure 4:
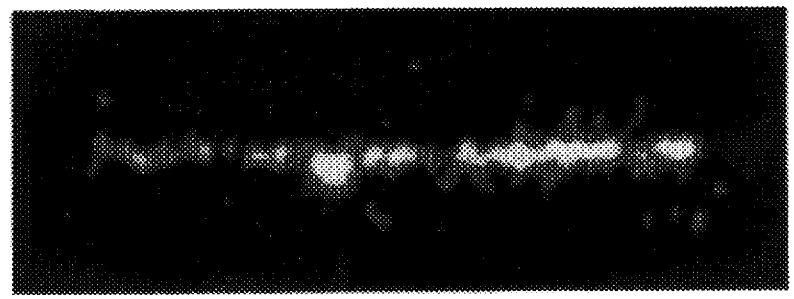
FIG. 4 shows the stained portion of a DIRVISH stained chromosome using a random sequence primer amplified biotinylated pulsed field gel purified 500 Kb YAC DNA probe.

The inventors have made biotinylated probes from a YAC by a random sequence primer amplification of pulsed field gel purified 500 Kb YAC DNA. When this probe is hybridized to extended human genomic DNA for DIRVISH DNA mapping, a stretch of fluorescein signal can be observed (FIG. 4). This image is a digital image taken from an American Innovision imaging system. The DNA forms a straight line with virtually no gaps, indicating that there are no large deletions in this YAC. This technique is thus suitable for mapping YACs in the same manner as demonstrated for cosmids.

Mapping YACs by DIRVISH DNA mapping.

The inventors have demonstrated the use of a 500 Kb YAC probe to label a strand of extended human genomic DNA as shown in FIG. 4. Studies have also showed how probes from restriction fragments and cosmids can be visually mapped to determine overlap, gap distance and orientation of the probes. First, YAC probes are mapped in the same manner as described for the cosmids. YAC probes isolated from eight different contigs identified by their known STS (sequence tagged sites) markers from human chromosome 3 as may additional YACs probes from new STS markers. These YACs, isolated from a CEPH library, have insert sizes of 400 to 800 Kb. Their positions on chromosome 3 have been mapped by FISH on metaphase chromosomes.

Figure 5:
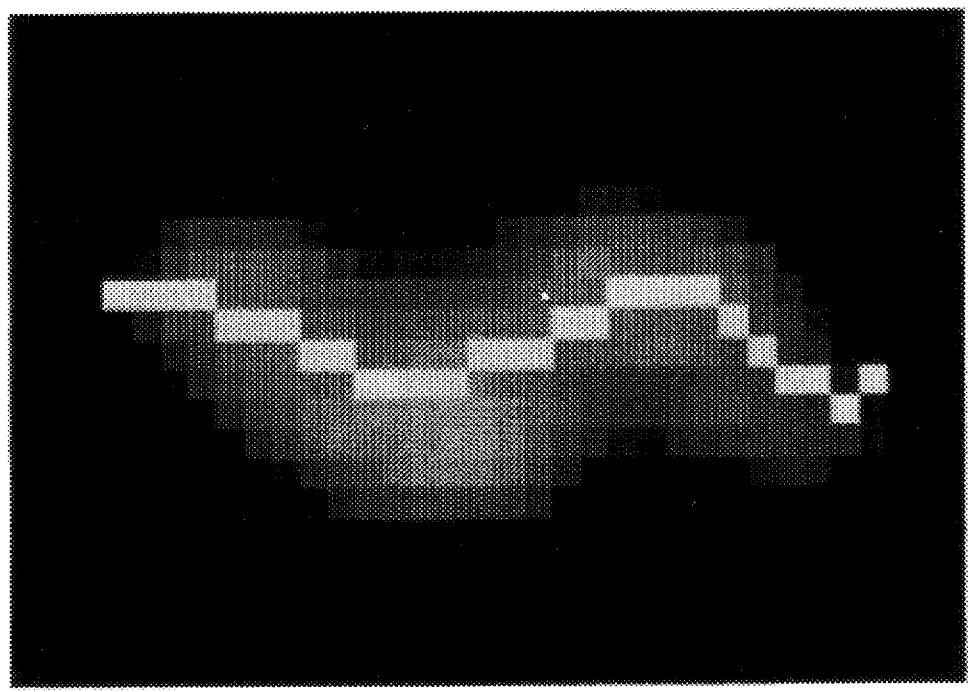
FIG. 5 shows a digitized image of a chromosome and the midline analysis of the DNA contour.

The general approach is to select three or more YACs containing each STS marker, which have the following characteristics: large YACs based on electrophoresis, maps by FISH to the same region on chromosome 3 (FIG. 5), and are not chimeras as judged by evidence of hybridization to a non-chromosome 3 location. Probes from the YACs are generated by a random hexamer primer amplification step, as used for the DIRVISH DNA YAC mapping. One YAC probe is then labelled with biotin-dUTP, one with digoxigenin-dUTP, and one with an equal mix of the two conjugated dUTPs. 200 ng of each labelled YAC probe is mixed with 10 µg of sheared human genomic DNA (used as a competitor for repetitive sequences) and hybridized to extended DNA from human primary fibroblast cells or human lymphocytes. DNA streams from lymphocytes are compared with fibroblasts initially to determine the best source of DNA. DNA streams are prepared as previously described. Approximately 200 cells are lysed on a glass slide and the drop of cellular DNA allowed to run down the slide thus forming the DNA stream.

The DIRVISH DNA map of three YACs is expected to appear as a long string with overlapping, contiguous stretches of red (digoxigenin), green, (biotin) and yellow (biotin plus digoxigenin) signal. All three YACs will overlap to some extent and only two of the starting colors can be observed in pure form at the ends of the contig. All other colors are derived from combinations of red, green and yellow due to probe overlap. These combinations of colors are used to deduce the extent of overlap between the three YACs. One combination of colors from YAC overlap which requires extensive deduction is the combination of the red and green to generate yellow. Since one of the YACs will already be labelled yellow, there can be some confusion as to which yellow signal represents the overlap versus the one YAC. When the combinations of colors prove to be too difficult to interpret then two YAC—two color DIRVISH DNA maps are used.

DIRVISH DNA map images are selected for analysis based on the appearance of the DNA, i.e., its extension and whether or not it appears to be intact. Ideally, images that stay within one field of view are analyzed. The DNA streaming procedure provides a gradient of extensions from super-extended (twice that for fully relaxed DNA) to highly condensed (comparable to DNA in the nucleus). The largest field of view is 200 µm across. A 1 Mb region conceivably spanned by 2 YACs would have to be extended no more than 59% of fully extended DNA to fit in the field and would be the maximum extension analyzed. At this level of extension the resolution of analysis is estimated at 2 Kb.

EXAMPLE 2

ANALYSIS OF LABELLED DNA

The DIRVISH DNA maps are analyzed using a color digital imaging systems from American Innovision and a 1–5X zoom lens coupler. Initially, software for simple tracking of the strands was used. Currently, only one color set is recognized and tracked at a time. For each different color set (i.e., red, green or yellow) the computer must be instructed with the appropriate first color to follow, then the subsequent colors, followed by a complete tracking. In order to avoid inaccuracies, particularly due to subjective user definable color recognition several maps may be compared.

Interpretation of the DIRVISH DNA maps requires that one probe (arbitrarily chosen) be used as a size reference in each hybridization. The size of the reference probe is previously determined by gel electrophoresis. Only YACs with contiguous or near contiguous signal are used as a reference. For example, if an overlap distance equivalent to 10% of the length of 1,500 Kb reference YAC is observed, then the overlap equals 50 Kb. Generally, all YACs in a hybridization with a known size can be used for reference. YACs that have a consistent size gap in signal in a consistent position are recorded as potentially having a deletion in this position.

From these data a map of each YAC within a contig is determined. The YACs that span the greatest distance are recorded for use in connecting contigs. Two or more contigs that map close to each other by metaphase and interphase FISH mapping are then mapped by DIRVISH DNA mapping. The two YACs that constitute the farthest ends of one contig are mapped with respect to two YACs from a neighboring contig. The orientation, gap distance or overlap are determined.

In cases where chromosome walking may be called for to fill a gap between two neighboring contigs, DIRVISH DNA mapping is used to avoid random walking by determining orientation. Probes derived from the YAC-vector linked ends of a YAC are mapped by DIRVISH DNA mapping to determine which end probe is proximal to the next contig YAC and thus suitable for use in directional chromosome walking.

II. Improving DIRVISH DNA Mapping Technology

The description of a 12 color fluorescent chromosome painted procedure (Duawerse, et al., (1990)) has made clear the versatility and speed of fluorescent labelling of probes with mixes of different fluorochromes. Using fluorescein-dUTP (green), rosorufin-dUTP (red) and hydroxycoumarin-dUTP (blue) from Boehringer-Mannheim Biochemicals or comparable nucleotides from Amersham, YAC DNA are fluorescently labelled directly. A triple band-pass filter is used to visualize all three fluorochromes simultaneously.

The ability to detect and map a large number of probes from YACs, cosmids and restriction fragments is useful in mapping a series of YACs within expanded contigs as well as gap distance to the next contig, mapping a series of cosmids will respect to themselves and within YACs, and mapping restriction fragments which, in addition, can help in determining orientations of multiple YACs or cosmids. Ultimately, this procedure produces a detailed multi-color map of a gene or DNA region making possible the rapid and precise detection of gene rearrangements. The principle of this labelling procedure is that when various combinations of fluorescein, rosorufin, and hydroxycoumarin (representing the fluorescent colors of green, red and blue, respectively) are mixed, a large number of distinguishable colors and probes are possible. Direct fluorescent labelling is preferred for two reasons: 1) it is faster than the indirect fluorescent labelling procedure (e.g., biotin labelling), and 2) there are a higher resolution of color mixing than with the indirect fluorescent labelling procedure. The mixing of biotin and digoxigenin in a probe as previously described in Example 1, results in a steric competition of binding of the fluorescent avidin or anti-digoxigenin Ab which can result in a crude and variable mix of red and green.

One disadvantage of using direct fluorescent probes is that detection is less sensitive than biotin (avidin plus amplification) procedure. Using standard FISH, the inventors have observed about a 10-fold reduction in sensitivity using fluorescein labelled probes versus biotin labelled probes (with avidin detection). To overcome the reduced sensitivity, longer exposure times on the color CCD camera are used. Presently, using the standard DIRVISH DNA mapping, a 1/3 second exposure is usually sufficient to visualize the images. Therefore, to capture a image with 10-fold less intensity, a 3 second exposure is necessary. The American Innovision imaging system uses an added cooled color CCD camera. Exposures up to 3 minutes are possible with this system without background (dark noise) or synchronization problems. Therefore, even if exposures longer than 3 seconds are needed, there should be no problem with imaging. The resulting images are determined by signal tracking.

EXAMPLE 3

Signal Tracking and Color Recognition

The approach of the present invention is to track down the center of an extended signal, e.g., a chromosome (see FIG. 2), and determines the midline length. The midline distance of the overall DNA contour is used to determine the length of chromosome 3 and the fractional length for the YAC probe hybridization sites. This system first recognizes one user definable color array that is set to encompass the signal throughout the object. Improvements are directed toward increasing the resolution and accuracy of signal tracking, and adding multi-color recognition to the program so as to distinguish between the different probes.

The current signal tracking program written in J language, is the language used for controlling the American Innovision system's image buffer. The program uses a set of rules to decide which direction it needs to proceed in order to accurately track the midline length of the object. A graphic representation of a small object in FIG. 1 is shown where the image is magnified to see square pixels that define the image.

Figures 2A, 2B:
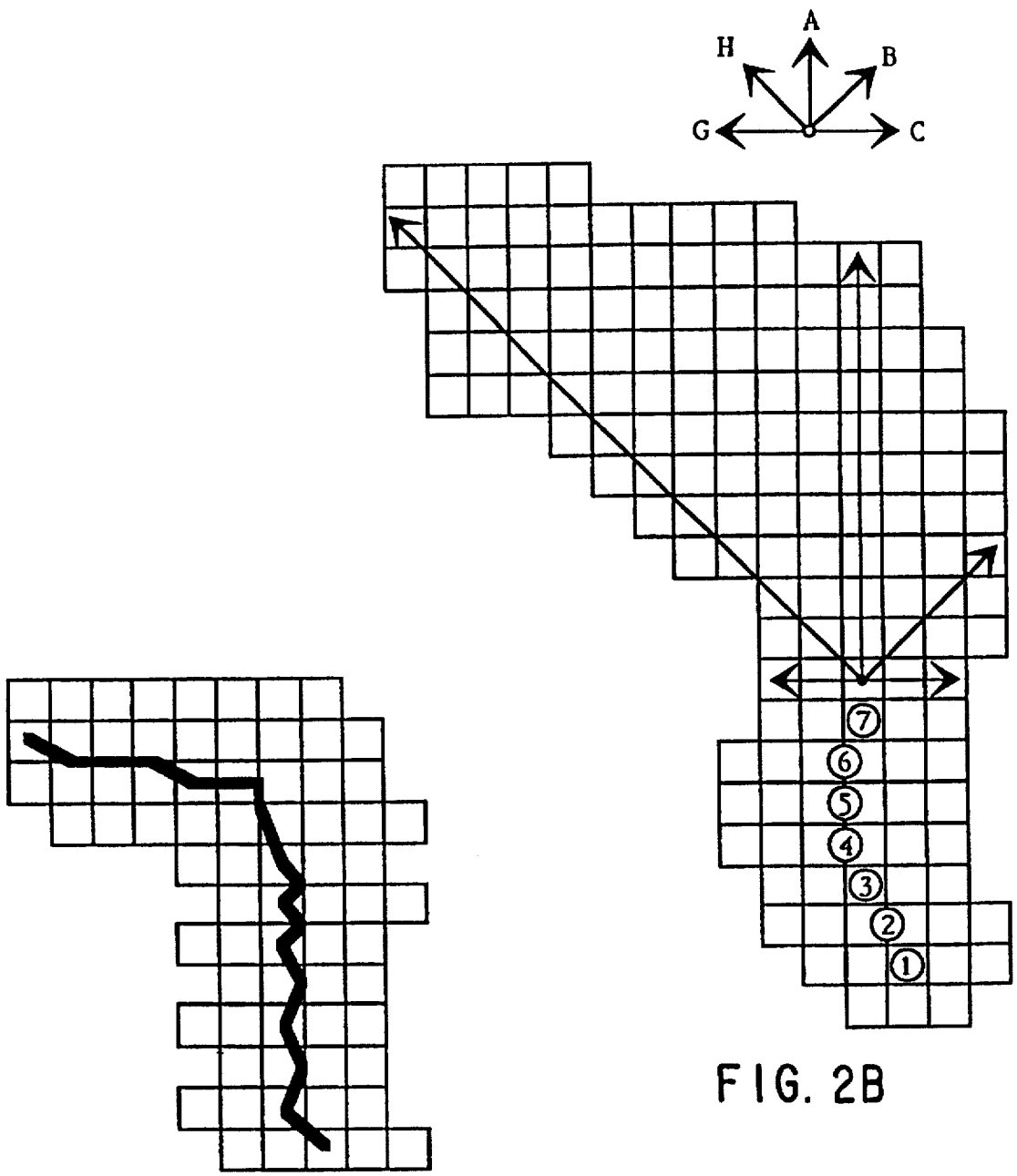
FIGS. 2A and 2B show the diagramatical representation of the image after seven midpoint determinations have been made.

The program initially evaluates the pixels along 8 vectors (A to H, see FIG. 1), the color in the pixels along the vectors, and their length. The longest vector is determined and this defines the direction of advancement. The objects to be analyzed must first be digitized and defined on a computer screen by pixels (as seen in FIG. 1 and 2). A range of colors that make up the object is defined by the user. A pixel position on the object is marked by the user using a mouse and cursor arrow. This pixel provides the starting point for the analysis. Initially, contiguous pixels in eight directions (A–H; see FIG. 1) are analyzed for the color range of the object (more directions provide a higher resolution analysis). The last pixel along the contiguous pixels for each direction is determined. The lengths from these eight pixels' coordinate positions to the starting pixel coordinate position is determined mathematically. The direction with the greatest distance is determined (for FIG. 1, direction A has the greatest distance). The last coordinate positions of the last pixels within the object along the perpendicular directions to direction A, i.e., directions C and G, are used to mathematically determine a midpoint.

The color values of the pixels along the two perpendicular directions are analyzed statistically and the average of these color values is recorded along with the midpoint analyzed statistically and the average of these color values is recorded along with the midpoint coordinate position. From the pixel closest to the midpoint position (which can be a fraction of a pixel) a new pixel is chosen by advancing to the next contiguous pixel in the direction previously determined to have the greatest distance (in this example, direction A). From this new position five directions (A, B, C, G, and H) are analyzed for contiguous colored pixels, and the direction with the greatest distance is determined. The midpoint of the perpendicular directions and the averaged color is calculated and recorded. This second set of analyses using the five directions completes the cycle that is used to throughout the rest of the object.

Turns are executed by detecting a new direction with a distance that is greater than that of the previous direction (see FIG. 2). FIG. 2 shows the analysis after determining 7 points along the object. At this point of the analysis a new direction (direction H) is found to have a greater distance than the previous direction A. The direction of progression now changes to direction H and the midpoint and colors for the directions perpendicular to direction H (i.e., directions B and F) are determined and recorded. Once the analysis has progressed to the end of the object, the other end of the object is analyzed starting from the initial starting position and evaluating directions C–G for the direction with the greatest distance.

The data recorded can be analyzed in a variety of ways. Typically the linear distance from midpoint to midpoint is mathematically determined and drawn on the computer screen along with the colors corresponding to the positions. This provides a linear representation of the object in a form that the human eye can interpret and evaluate, termed the midline. The data is also plotted to show a graphic representation of the values of distance and color obtained from the object. Thus no recognition of color is needed since it can be objectively observed graphically. Based on determining mathematical centers and distances between points, the midline length is invariably a fractional pixel distance.

Turning corners to follow the contour is accomplished by detecting a change in the longest vector. As shown in FIG. 1, at pixel 6, the longest vector has changed to D, thus indicating a turn to the left. The distance and centerpoint of the perpendicular vectors is not immediately determined. The angle of the vector used in these measurements are slowly changed (one pixel at a time) from A and E until vectors B and F are reached. Then the analysis continues in the direction of vector D, analyzing vectors B and F until a new longest vector is found indicating another turn. With this program, a 90° turn is broken up into two separate 45° turns.

Additional vectors may be used to more precisely navigate through turns. Though tracking through turns is apparently not critical for the straight lines of DIRVISH DNA maps observed over hundreds of Kb, it will likely become important as DIRVISH DNA mapping extends over the Mb range, and for FISH analysis. The inventors have found that the use of vectors B, C, G, and H are necessary for tracking most turns, in this example. However, sometimes navigation through series of tight turns is not possible. The use of more vectors helps to identify the direction of tight turns. Vectors at angles of 26.5° and 63.5° to the X axis are used in addition to the 45° angle vectors. Test signals are used to evaluate tracking and distance measurements to determine the necessity of the added vectors.

A more important development is the recognition of color throughout the length of the DNA strands in the DIRVISH DNA maps. The American Innovision imaging system uses a unique color model where color is divided into intensity and a combination of hue and saturation. A z-axis scale of 0 to 255 defines the intensity. X-Y coordinate of 255, 0 equals red and 100% saturation and 0, 255 equals blue with 100% saturation. The closer the coordinate is to the center (at 199, 199) of the X-Y scale, the lower the saturation.

The American Innovision imaging system is capable of simultaneously evaluating nine color arrays. The color coordinates are recorded for each color recognized by the eye and a probe name assigned to each array. Color coordinates are evaluated along the two vectors perpendicular to the longest vector (i.e., the same vector as used for determining the centerpoint). Thus, for each point recorded an average of the color coordinates is assigned. When a new color array representing one of the other colors is encountered, the position along with object is recorded and the average of the new color coordinates are assigned to that point. This continues for the length of the object.

Gaps in signal are first handled by user intervention to jump over the gap to the next signal in line. A line drawn between the last point of other previous signal and the first point of the next signal decreases the precision of the distance determination, since there is no way to know the correct midline length that exists for the DNA strand in the gap region where there is no contour. An automated gap jumping routing can broaden the scan for new signal starts where the last signal ends, continuing in the direction it previously pursued. When the next signal is found, the first point is found and a line drawn across the gap. The broad band scan will be ineffective for large gaps where the DNA makes a sharp turn, therefore, user intervention may occasionally be required.

All data recorded from the above analysis are stored in an ASCII file to be read after the analysis. From the data, a linear graphic representation is drawn and a distance calibration step measures the length of the control YAC and records the YAC size in Kb. The graphic representation includes the length of a particular color array (e.g., red), with one pseudocolor for all points within that color array. Alternatively, actual color assigned to each point may be generated. This will show color variation throughout a probe's signal. The graphic representation may also have the probe name printed below the appropriate stretch of color, the position and lengths of each color, as well as black indicating a gap's position and length.

A routine that reduces user intervention in assigning colors for each probe relies on a consistent and objective computer program. This requires the analysis of the distribution of all color coordinates within the DIRVISH DNA map. The result would be clusters of 3 dimensional coordinates that are distinct from one another. However, the greater the numbers of colored probes, the greater the chance of cluster overlap. From the signal tracking, the average color coordinates for each point along the DNA strand are evaluated as to which color coordinate cluster it belongs, and thus which probe the computer is analyzing and tracking.

In addition to a graphic representation of each DIRVISH DNA map, an average of the data from each map is determined, in order to generate a consensus map. In cases where there is the potential for heterogeneity in map structure, the user will compare the maps to determine if there is more than one map present. Heterogeneity is not likely for the DIRVISH DNA mapping of cloned YACs, greatly enhancing the precision of the maps.

EXAMPLE 4

ANALYSIS OF DIRVISH DNA

This example illustrates use of the invention for analyzing DIRVISH data. However, for chromosome-specific paints, the programs will distinguish between the different chromosomes, and with further software development, it is contemplated that a computer will automatically generate karyotype based on fluorescence.

Figure 6A:
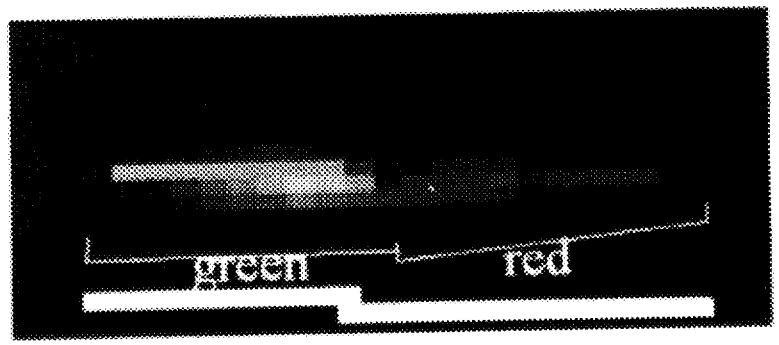
FIGS. 6A and 6B are a DIRVISH string, shown with a 7.3 Kb probe in red (rhodamine) and a 4.8 Kb probe in green (fluorescein).
Figure 6B:
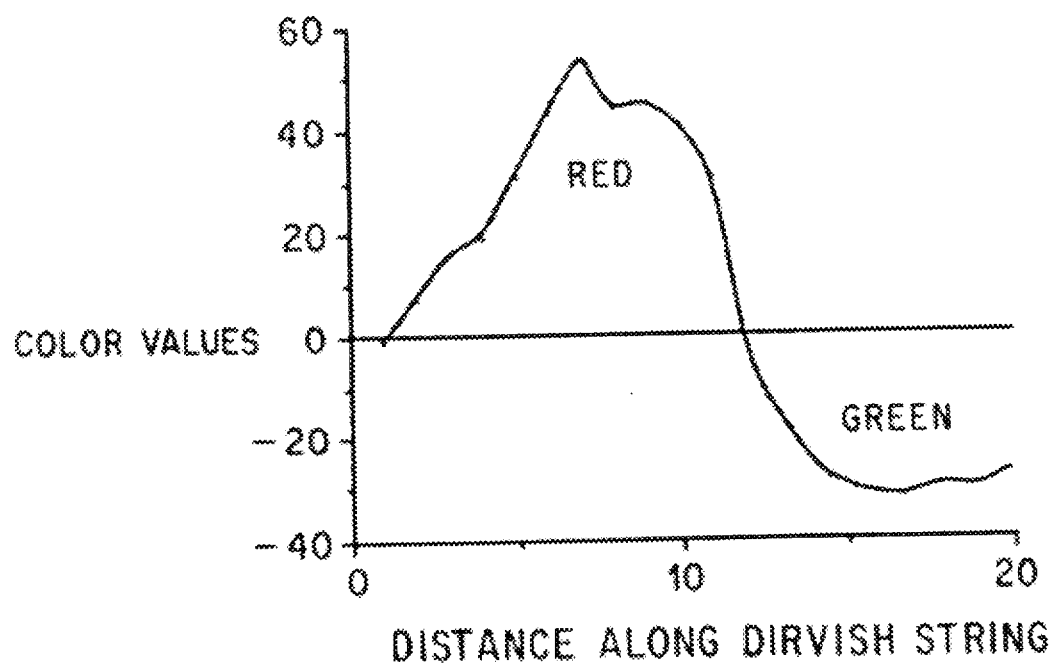

A DIRVISH string with a 7.3 Kb probe in red (rhodamine) and a 4.8 Kb probe in green (fluorescein) is shown in FIG. 6. The string of signal was analyzed for color and coordinate position. A tracing line, shown below it, shows how the string of signal was traced. A graph of the one dimensional color values customized for red to green analysis only, is shown.

Figure 7A:
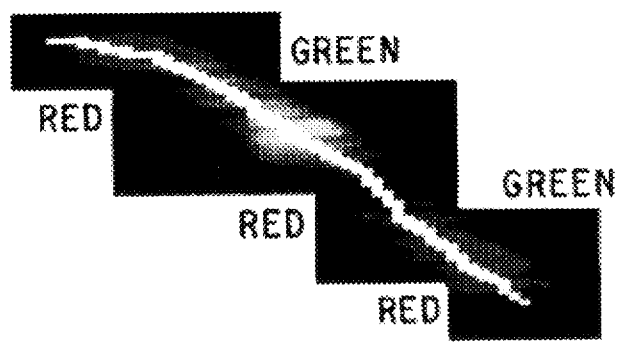
FIGS. 7A and 7B show a comparative genomic hybridization (CGH) performed on normal chromosomes using tumor DNA as a probe (green) and normal DNA (red) as a control. The chromosome shown in FIG. 7A represents significant rearrangement in the tumor cells as seen by the variable regions of red and green. This can be seen from the analysis of color and coordinate positions. The graph in FIG 7B shows three large regions that are primarily red and two large regions that are primarily green.
Figure 7B:
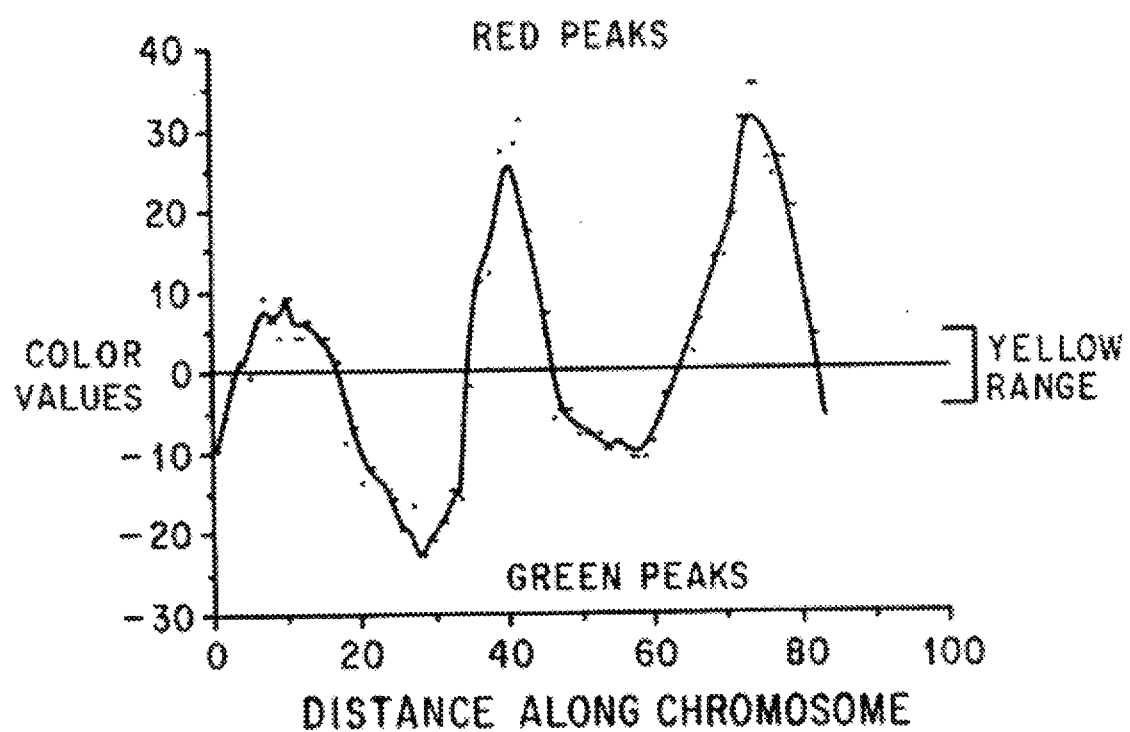

A comparative genomic hybridization (CGH) was performed on normal chromosomes using tumor DNA as a probe (green) and normal DNA (red) as a control (FIG. 7). The chromosome shown has significant rearrangement in the tumor cells as seen by the variable regions of red and green. This can be easily seen from the analysis of color and coordinate positions. The graph shows three large regions that are primarily red and two large regions that are primarily green.

To further demonstrate the application of the present invention in conjunction with FISH DNA mapping over longer distances, and its application to studying biologically significant rearrangements, the structure of an amplified gene locus was determined. Determining the structure of amplified genes has proven valuable in elucidating the mechanism of their formation. However, using standard cloning and restriction mapping techniques, this characterization is usually a difficult and time-consuming process. This is particularly true because of the repetitive and complex nature of amplification arrays.

A DIRVISH DNA map of an amplified DHFR locus in a hamster cell line was generated. These cells were previously shown by FISH analysis of metaphase chromosomes to contain approximately 8 DHFR genes clustered at the end of one chromosome (Windle, et al., 1991). The spacing between the amplified DNA units and the arrangement of DHFR genes cannot be determined by standard FISH analysis. The size of the largest amplicon is calculated to be ~46 Kb. The configuration of the array from DIRVISH DNA map data indicated a combination of direct and inverted repeats. There is considerable diversity in the apparent amplification structure as judged by the diversity in the DIRVISH DNA maps of individual structures. This diversity in structure and the subtle rearrangements observed normally escape detection and characterization when standard restriction mapping and cloning methods are used.

The mapping of another amplified DHFR structure in hamster cells, determined by restriction mapping of cosmid contigs, was previously shown to have amplified units ~270 Kb with a mix of inverted and direct repeated units. In such a study, a DIRVISH DNA map provided similar types of information within 2 days with data that was much easier to interpret.

EXAMPLE 5

Application of DIRVISH DNA Mapping to a YAC Clone of Human DNA

The present invention is useful in analyzing a 500 Kb YAC probe to determine if there are deletions. For example, a 500 Kb YAC containing DNA from the NF1 region of human chromosome 17 was obtained from Dr. Peter O'Connell, University of Texas Health Science Center at San Antonio, Dept. of Pathology, Tex. (Viskochil, et al. 1990; Wallace, et al. 1990). The YAC probe was labelled with biotin and visualized with fluorescein labelling. The analysis of the DIRVISH DNA map appears as a contiguous signal covering the length of the YAC. This indicated that there were no deletions, which if present would appear as a gap in the signals.

Considerably more utilities are encompassed based on the present invention. For example, exploring a large number of vectors for analysis, and evaluating color using statistical models to distinguish between colors. The invention analyzes images and patterns in the same way and with comparable sensitivity to the human eye.

EXAMPLE 6

This example illustrates the use of DIRVISH technology to detect, identify and map origins of replication and origins of termination.

Mapping and Determination of orientation of Replication

A pulse of biotin-dUTP was incorporated into a spread of DNA linearized by the procedures of Example 1. This was followed by a pulse of digoxigenin-dUTP. Replication origins were visualized by fluorescein and rhodamine detection of the labeled nucleotides. A replication origin appeared as a stretch of green signal (fluorescein) flanked on both sides by stretches of red signal (rhodamine). The center of the green signal represented the initiation site of replication or the origin. DIRVISH mapping of this DNA with a probe pinpointed the origin that was linked to the probed DNA region. The exact position of the origin was mapped by measuring the distance from the probe to the origin using the probe length as a size reference.

EXAMPLE 7

It is contemplated that the invention will be useful for detecting the effects of drugs on cells that harbor oncogenes or drug-resistance genes. Selective inhibition can be observed by showing that the length of replicating DNA on the extrachromosomal DNA is shorter than the length of replicating DNA near a control region on a chromosome, or that replicating DNA is found less frequently on the extrachromosomal DNA than near the control region.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that one might map positions of repeats on DNA strands to determine repeat polymorphisms between individuals, determination of the structure of very large genes such as the Duchennes Muscular Dystrophy gene, use of probes from NotI linking or jumping libraries to place NotI sites on a DIRVISH DNA map or detection of site-specific breaks. All such similar applications, as well as other variations in producing extended or super-extended DNA apparent to those skilled in the art are deemed to be within the spirit, scope and concept of the invention as defined by the appended claims. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bellanne-Chantelot et al. (1992). *Cell* 70:1059–1068.
Botstein, D., White, R. L., Skolnick, M. and Davis, R. W. (1980) *Am. J. Hum. Genet.* 32:314–331.
Burke, D. T., Carle, G. F. and Olson, M. V. (1987) *Science* 236:806–812.
Burmeister, M. and Lehrach, H. (1986) *Nature* 324:582–585.
Cangiano, G., Ameer, H., Waterston, R. and La Volpe, A. (1990) *Nuc. Acids Res.* 18:5077–5081.
Coulson, A., Waterston, R., Kiff, J., Sulston, J. and Kohara, Y. (1988) *Nature* 335:184–186.
Deininger, P. L., Jolly, D. J., Rubin, C. M., Friedman, T. and Schmid, C. W. (1981) *J. Mol. Biol.* 151:17–33.
Duawerse et al. (1990). *Human Molecular Genetics* 8:593–598.
Evans, G. A. and Lewis, K. A. (1989) *Proc. Natl. Acad. Sci. USA* 86: 5030–5034.
Glazer, A. N., Peck, K. and Mathies, R. A. (1990) *Proc. Natl. Acad. Sci. USA* 87:3851–3855.
Goss, S. J. and Harris, H. (1975) *Nature* 255:680–684.
Greig, G. M., England, S. B., Bedford, H. M. and Willard, H. F. (1989) *Am. J. Hum. Genet.* 45:862–872.
Huberman, J. A. and Riggs, A. D. (1966) *Proc. Natl. Acad. Sci. USA* 55:599–606.
Korenberg, J. R. and Rykowski, M. C. (1988) *Cell* 53:391–400.
Kyte & Doolittle (1982) *J. Mol. Biol.* 157:105–132
Lawrence et al. (1990). *Science* 249:928–932.
Leach, R. J., Thayer, M. J., Schafer, A. J. and Fournier, R. E. K. (1989) *Genomics* 5:167–176.
Lichter, P., Ledbetter, S. A., Ledbetter, D. H. and Ward, D. C. (1990) *Proc. Natl. Acad. Sci. USA* 87:6634–6638.
Lichter, P., Tang, C. J., Call, K., Hermanson, G., Evans, G. A., et al. (1990) *Science* 247:64–69.
Litt, M. and Luty, J. A. (1989) *Am. J. Hum. Genet.* 44: 397–401.
Kallioniemi et al. (1992). *Science* 258:818–821.
Moyzis, R. K., Buckingham, J. M., Cram, L. S., Dani, M., Deaven, L. L., et al. (1988) *Proc. Natl. Acad. Sci. USA* 85:6622–6626.
Moyzis, R. K., Torney, D. C., Meyne, J., Buckingham, J. M., Wu, J. R., et al. (1989) *Genomics* 4:273–289.
Nakamura, Y., Leppert, M., O'Connell, P., Wolff, R., Holm, T., et al. (1987) *Science* 235:1616–1622.
Paulson, J. R. and Laemmli, U. K. (1977) *Cell* 12:817–828.
Pinkel, D., Straume, T. and Gray, J. W. (1986) *Proc. Natl. Acad. Sci. USA* 83:2934–2938.
Poustka, A., Pohl, T. M., Barlow, D. P., Frischauf, A. M. and Lehrach, H. (1987) *Nature* 353:353–355.
Ruddle, F. H., Chapman, V. M., Ricciuti, F., Murnane, M., Klebe, R., et al. (1971) *Nature New Biology* 232:71–73.
Sambrook et al. (1989). Molecular cloning: A laboratory manual. Cold Spring Harbor Laboratory. Cold Spring Harbor, N.Y.
Sasaki, M. S. and Norman, A. (1966) *Exp. Cell Res.* 44:642–645.
Schmid, C. W. and Jelinek, W. R. (1982) *Science* 216:1065–1070.
Schwartz, D. C. and Koval, M. (1989) *Nature* 338:520–522.
Scott, A. F., Schmeckpeper, B. J., Abelrazek, M., Comey, C. T., O'Hara, B., et al. (1987) *Genomics* 1:113–125.
Stallings, R. L., Torney, D. C., Hildebrand, C. E., Longmire, J. L., Deaven, L. L., et al. (1990) *Proc. Natl. Acad. Sci. USA* 87:6218–6222.
Trask, B., Pinkel, D. and van den Engh, G. (1989) *Genomics* 5: 710–717.
van den Engh et al. (1992). *Science* 249:1410–1412.

Viskochil, D., Buchberg, A. M., Xu, G., Cawthon, R. M., Stevens, J., et al. (1990) *Cell* 62:187–192.

Wallace, M. R., Fountain, J. W., Brereton, A. M. and Collins, F. S. (1989) *Nuc. Acids Res.* 17:1665–1677.

Wallace, M. R., Marchuk, D. A., Andersen, L. B., Letcher, R., Odeh, H. M., et al. (1990) *Science* 249:181–186.

Waye, J. S. and Willard, H. F. (1986) *Mol. Cell. Biol.* 6:3156–3165.

Weber, J. L. and May, P. E. (1989) *Am. J. Hum. Genet.* 44:388–396.

Windle, B., Draper, B. W., Yin, Y., O'Gorman, S. and Wahl, G. M. (1991) *Genes Dev.* 5, 160–174 (1991).

Yagle, M. K., Parruti, G., Xu, W., Ponder, B. A. and Solomon, E. (1990) *Proc. Natl. Acad. Sci. USA* 87:7255–7259.

What is claimed is:

1. A Method of mapping an origin of replication, comprising:
   a) incubating a permeabilized cell by pulse chase with a replication buffer comprising ATP, dATP, dGTP, dCTP, dTTP and labeled dUTP to produce labeled DNA;
   b) isolating the labeled DNA from the cell;
   c) gravitationally stretching the labeled DNA;
   d) hybridizing the stretched DNA with a detectably labeled oligonucleotide probe that binds to said labeled DNA; and
   e) detecting the position of the labeled DNA which maps the origin of replication.

2. The method of claim 1 wherein the cell is a mammalian cell.

3. The method of claim 1 wherein the labeled dUTP is biotin-dUTP or digoxigenin dUTP or fluorescein dUTP.

4. The method of claim 1 wherein the chase is with unlabeled dTTP.

5. The method of claim 1 wherein the origin of replication is an origin site or a termination site.

6. The method of claim 1 wherein the detectably labeled oligonucleotide probe is labeled with digoxigenin.

7. The method of claim 1 wherein the detectably labeled oligonucleotide probe hybridizes within about 500 Kb of an origin of replication.

8. The method of claim 1 wherein the detectably labeled oligonucleotide probe is fluorescently labeled.

9. The method of claim 8 wherein the fluorescently labeled oligonucleotide probe is labeled with rhodamine or fluorescein.

10. A method of identifying termination site-specific inhibitor drugs, comprising:
    a) incubating a permeabilized cell by pulse chase with a replication buffer comprising ATP, dATP, dGTP, dCTP, dTTP, detectably labeled dUTP and a drug suspected of site-specifically inhibiting replication termination to produce labeled DNA;
    b) isolating the labeled DNA from the cell;
    c) gravitationally stretching the labeled DNA;
    d) hybridizing the stretched DNA with a detectably labeled oligonucleotide probe that binds to said labeled DNA; and
    e) detecting the position of the labeled DNA wherein more than one site of labeled DNA is indicative of a drug that inhibits site specific termination.

11. The method of claim 10 wherein the detectably labeled oligonucleotide probe is labeled with rhodamine or fluorescein.

12. A method of mapping DNA comprising:
    (a) extending DNA to a substantially linear form;
    (b) hybridizing a labeled probe to the substantially linear DNA;
    (c) generating a color image of the hybridized substantially linear DNA;
    (d) digitizing and storing the color image;
    (e) processing the stored color image to identify a midline of the hybridized substantially linear DNA; and
    (f) mapping the hybridized substantially linear DNA as a function of the identified midline.

13. The method of claim 12, wherein the color image of the hybridized linear DNA is generated using computer interfaced CCD cameras.

14. The method of claim 12, wherein the DNA is extended up to about 0.34 μm per kilobase pair.

15. The method of claim 12, wherein the DNA is super-extended between about 0.34 μm and 0.65 μm per kilobase pair without breakage of the DNA.

16. The method of claim 12, wherein the DNA is cellular DNA.

17. The method of claim 12, wherein the DNA is duplex or single stranded DNA.

18. The method of claim 17, wherein the duplex DNA is treated with a protein denaturant.

19. The method of claim 14 or 15, wherein the DNA is extended by gravitational streaming.

20. A method for determining physical distances along a DNA segment comprising:
    (a) extending DNA to form a substantially linear molecule;
    (b) labeling the linear DNA at spaced locations along the linear DNA by hybridization with a plurality of fluorescently labeled oligonucleotide probes;
    (c) producing a color image of the hybridized linear DNA;
    (d) storing a pixelized version of the color image; and
    (e) for each color in the color image, processing the color image to determine a midline of the image; and
    (f) calculating the length of the midline based on evaluating a plurality of pixels for colors emanating from a starting point and distance each vector extends within the color image.

21. The method of claim 20, wherein relative positions of the color image is displayed as a linear representation of the objects by plotting color values on a graph to show color variations.

22. The method of claim 20, wherein at least 2 vectors are evaluated.

23. The method of claim 20, wherein eight surrounding vectors are evaluated.

24. The method of claim 20, wherein between about 2 to 640 surrounding vectors are evaluated.

25. The method of claim 20, wherein the processing step (e) comprises the steps of:
    (a) selecting a starting point in the color image;
    (b) evaluating the pixels surrounding the starting point for colors along a plurality of vectors emanating from the starting point and the distance each vector extends within the color image;
    (c) determining a first longest said vector;
    (d) advancing along the first longest vector to a first midpoint of the color image along a line perpendicular to the first longest vector;
    (e) marking and storing the position of the first midpoint along with color values of pixels along the first longest vector;
    (f) repeating steps (a) through (e) wherein each successive midpoint serves as a new starting point until the border of the color image is reached; and
    (g) calculating the length of the midline based on all such midpoints.

* * * * *